United States Patent [19]
Feke et al.

[11] Patent Number: 5,633,695
[45] Date of Patent: May 27, 1997

[54] BEAM STEERING OPTICAL SYSTEM AND METHOD AND OPHTHALMIC APPARATUS USING SAME HAVING SPACED APART IRRADIATION AND OBSERVATION PATHS

[75] Inventors: Gilbert T. Feke, Stoneham; Francois Delori; Robert H. Webb, both of Lincoln, all of Mass.

[73] Assignee: Canon Kabushiki Kaisha, Tokyo, Japan

[21] Appl. No.: 515,067

[22] Filed: Aug. 14, 1995

[51] Int. Cl.$^6$ .................... A61B 3/10; A61B 3/00
[52] U.S. Cl. .................... 351/221; 351/205; 351/246
[58] Field of Search .................... 351/205, 221, 351/211, 210, 206, 246; 354/62

[56]        References Cited
        U.S. PATENT DOCUMENTS

| 4,856,891 | 8/1989 | Pflibsen et al. ............ 351/210 |
| 5,094,523 | 3/1992 | Reznichenko et al. ......... 351/211 |
| 5,106,184 | 4/1992 | Milbocker ................. 351/211 |

*Primary Examiner*—Hung X. Dang
*Attorney, Agent, or Firm*—Fitzpatrick, Cella, Harper & Scinto

[57] ABSTRACT

A beam steering optical system having a system pupil includes an irradiating optical system producing an irradiating light beam for irradiating an object. The system also includes a two-sided rotatable mirror positioned to cover only a first portion of the system pupil and to receive and reflect with a first surface the irradiating light beam. An objective lens receives the irradiating light beam reflected from the mirror and focuses the irradiating light beam on the object. These elements together define an irradiation path for the irradiating light beam. When reflected by the object, the irradiating light beam is denoted as a detecting light beam. The objective lens receives the detecting light beam reflected by the object and directs it to a second portion of the system pupil not covered by mirror. A beam redirector receives the detecting light beam after passing through the second portion of the system pupil, and redirects it to a second surface of the mirror, which reflects the detecting light beam to a position-sensing photodetector. The mirror steers both beams through the same angle when rotating. The objective lens, the mirror, the beam redirector, and the photodetector together define an observation path for the detecting beam. The irradiation path and the observation path are spaced from each other to prevent cross-talk therebetween.

14 Claims, 7 Drawing Sheets

BEAM STEERING OPTICAL SYSTEM AND METHOD AND OPHTHALMIC APPARATUS USING SAME HAVING SPACED APART IRRADIATION AND OBSERVATION PATHS

BACKGROUND OF THE INVENTION

1. Field of the Invention

The present invention relates to a beam steering optical system. More particularly, the present invention relates to an optical system for steering or redirecting light beams in forward and reverse directions through an objective lens and a steering optical system. The present invention is also directed to an ophthalmic apparatus using such a beam steering optical system.

2. Description of the Related Art

In optical devices, such as scanning laser microscopes, an irradiating beam for irradiating the eye is directed along an irradiating path to x and y axis steering mirrors before being focused at a target within the eye. A detecting beam reflected from the target is imaged back along substantially the same irradiating path to the x and y axis steering mirrors before it is split off from the irradiating path and directed to a photodetector or an imaging device. More generally, an optical system used in a clinical setting may require one or more irradiating beams and one or more detecting beams to be all steered together using one or more mirrors. In such a system, the irradiating beam may be a diagnostic probing beam such as the red beam of a laser Doppler instrument, or a treatment beam, such as a point-focused surgical laser beam. Direct illumination of the eye may also be provided independently of the steering mirror or mirrors, for example, by flooding the eye with sufficient light to view the field of clinical interest in the eye. The detecting beam or beams reflected by the eye may be focused to produce a visual image, converted by a photodetector to a localized tracking image signal, converted to a tissue reflectance value used for laser intensity control, or processed in some other way. In such instruments, it is desirable for the treatment light beam and the detecting light beam to pass through steering mirrors to vary the field of treatment or observation, respectively.

One instrument of this type is described in U.S. Pat. No. 4,856,891. This patent discloses an eye fundus tracker/stabilizer using a common steering system to steer a narrow diagnostic or treatment light beam toward the eye and to receive light returning from the eye as a return image. The advantage of such a beam steering system is that by moving a steering mirror or mirrors to stabilize the position of the return image, the diagnostic or treatment light beam incident on the eye is automatically maintained at a stable location on the eye fundus bearing a fixed spatial relationship to the imaged area. However, when such a system is used to observe or treat a target on the fundus of an eye, the relatively intense diagnostic or treatment light input into the instrument to irradiate the eye scatters in the steering assembly, adding substantial noise to the extremely weak light returning from the eye. In addition, when it is desired to position a steering mirror and one or more stops confocal with the observed field or with the pupil of the eye, precision is required in locating or aligning the beam with respect to these elements. This structure complicates the problem of maintaining sufficiently distinct paths for the input light and the return light, and further compounds the noise and cross-talk problems.

U.S. Pat. Nos. 5,094,523 and 5,106,184 propose solutions to these problems. These patents disclose a two dimensional light steering apparatus comprising a pair of pivotable beam-directing elements, each having first and second faces. A beam traveling in a first direction is redirected by the first face of both elements, and a beam traveling in the second direction is redirected by the second face of both elements. The elements are preferably relatively thin planar mirrors (so called two-sided mirrors) which each steer the light about one of two axes. The first and second faces each perform a virtually identical purely pivotal steering motion to provide a wide field scan which is not occluded by system pupils. Steering in two dimensions may be employed for irradiating an eye and detecting light reflected therefrom through a common objective lens assembly. This structure allows highly efficient and jitter-free imaging, while providing effective input/output beam separation for such difficult applications as simultaneously treating and imaging the fundus of the eye.

However, the apparatus disclosed in U.S. Pat. Nos. 5,094,523 and 5,106,184 is complicated because they are designed for two-dimensional beam steering and two-dimensional imaging. For example, the irradiating beam path and the detecting beam path cross each other in the beam steering optical system. This limits one's flexibility in aligning the optical elements comprising the steering optical system itself and other systems such as the irradiating optical system (which produces a suitable shape for the irradiating beam) and the light detecting optical system which contains stops and detectors. Such a complicated structure is not needed for one-dimensional beam steering, used, for example, in a laser Doppler instrument for measuring retinal vessel blood flow.

Thus, there is a need for a beam steering optical system and an ophthalmic instrument using beam steering that is simple in structure which generates little noise and cross-talk between an irradiating beam irradiating the eye and a detection beam reflected by the eye. There is also a need for a beam steering optical system and an ophthalmic instrument using beam steering that maintains distinct paths for the irradiating light and the detecting light. In addition, there is a need for a one-dimensional beam steering apparatus which generates low amounts of noise and little cross-talk between an irradiating beam irradiating the eye and a detection beam reflected by the eye.

SUMMARY OF THE INVENTION

It is an object of the present invention to overcome the problems noted above.

It is another object of the present invention to provide a beam steering optical system and an ophthalmic instrument using beam steering that is simple in structure which generates little noise and cross-talk between an irradiating beam irradiating the eye and a detection beam reflected by the eye.

It is still another object of the present invention to provide a beam steering optical system and an ophthalmic instrument using beam steering that maintains distinct paths for the irradiating light and the detecting light.

It is a further object of the present invention to provide a one-dimensional beam steering apparatus which generates low amounts of noise and little cross-talk between an irradiating beam irradiating the eye and a detecting beam reflected by the eye.

According to one aspect, the present invention which achieves one or more of these objectives relates to a beam steering optical system having a system pupil. The system comprises an irradiating optical system, a two-sided rotatable mirror, an objective lens, beam redirecting means, and a position-sensing photodetector. The irradiating optical system produces at least one irradiating light beam for irradiating an object. The two-sided rotatable mirror is positioned to cover only a first portion of the system pupil and to reflect with a first surface the at least one irradiating light beam received from the irradiating optical system. The objective lens is positioned to receive the at least one irradiating light beam reflected from the two-sided rotatable mirror and to focus the at least one irradiating light beam on the object.

The irradiating optical system, the two-sided rotatable mirror, and the objective lens together define an irradiation path for the at least one irradiating light beam. In addition, the objective lens, the two-sided rotatable mirror, and the photodetector together define an observation path for the at least one detecting light beam.

The photodetector is positioned to receive at least one detecting light beam comprising the at least one irradiating light beam reflected by the object and then by a second surface of the two-sided rotatable mirror. The beam redirecting means redirects one of the at least one irradiating light beam and the at least one detecting light beam.

The irradiating optical system and the photodetector are positioned so that one of the following two arrangements occurs. In a first arrangement the at least one detecting light beam reflected by the object passes through the second portion of the system pupil not covered by the two-sided rotatable mirror to the beam redirecting means. The beam redirecting means redirects the at least one detecting light beam to the second surface (nearer to the photodetector) of the two-sided rotatable mirror. The second surface of the two-sided rotatable mirror then reflects the at least one detecting light beam to the photodetector. In a second arrangement the at least one irradiating light beam is reflected by the first surface (nearer to the light source) of the two-sided rotatable mirror to the beam redirecting means. The beam redirecting means redirects the at least one irradiating light beam through a second portion of the system pupil not covered by the two-sided rotatable mirror and then through the objective lens to the object.

By interchanging the light source of the irradiating optical system and the photodetector, the observation path and the irradiation path can be reversed, and the first arrangement can be changed to the second arrangement and vice versa.

The two-sided rotatable mirror steers both the at least one irradiating light beam and the at least one detecting light beam through the same angle when the two-sided rotatable mirror rotates. In order to prevent cross-talk between the at least one irradiating light beam and the at least one detecting light beam, the irradiation path and the observation path are spaced from each other at least at the system pupil.

According to another aspect, the present invention which achieves one or more of these objectives relates to an ophthalmic apparatus comprising an irradiating optical system, a beam steering optical system, an objective lens, and a detecting optical system.

The irradiating optical system comprises at least one light source producing at least one irradiating light beam for irradiating an eye. The objective lens is positioned to receive the at least one irradiating light beam to focus the at least one irradiating light beam on the eye. The detecting optical system comprises at least one photodetector, and receives at least one detecting light beam comprising the at least one irradiating light beam reflected by the eye. The beam steering optical system has a system pupil and comprises a two-sided rotatable mirror and beam redirecting means.

The two-sided rotatable mirror is positioned to cover only a first portion of the system pupil and to reflect with a first surface thereof the at least one irradiating light beam received from the irradiating optical system. In addition, the two-sided rotatable mirror reflects to the at least one photodetector with a second surface thereof the at least one detecting light beam reflected by the eye.

The beam redirecting means redirects one of the at least one irradiating light beam and the at least one detecting light beam. The irradiating optical system and the at least one photodetector are positioned so that one of the following two arrangements occurs. In the first arrangement the at least one irradiating light beam is reflected by the first surface of the two-sided rotatable mirror to the beam redirecting means. The beam redirecting means redirects the at least one irradiating light beam through a second portion of the system pupil not covered by the two-sided rotatable mirror and then through the objective lens to the eye. In the second arrangement the at least one detecting light beam reflected by the eye passes through the second portion of the system pupil not covered by the two-sided rotatable mirror to the beam redirecting means. The beam redirecting means redirects the at least one detecting light beam to the second surface of the two-sided rotatable mirror. The second surface of the two-sided rotatable mirror reflects the at least one detecting light beam to the at least one photodetector.

In this embodiment the objective lens makes the pupil of the eye conjugate with the system pupil. In addition, the irradiating optical system, the two-sided rotatable mirror, and the objective lens together define an irradiation path for the at least one irradiating light beam. Also, the objective lens, the two-sided rotatable mirror, and the detecting optical system together define an observation path for the at least one detecting light beam.

By interchanging the light source of the irradiating optical system and the photodetector, the observation path and the irradiation path can be reversed, and the first arrangement can be changed to the second arrangement, and vice versa.

The two-sided rotatable mirror steers both the at least one irradiating light beam and the at least one detecting light beam through the same angle when the two-sided rotatable mirror rotates. In order to prevent cross-talk between the at least one irradiating light beam and the at least one detecting light beam, the irradiation path and the observation path are spaced from each other at least at the system pupil.

According to another aspect, the present invention which achieves one or more of these objectives relates to a beam steering method for steering a beam in a beam steering system having a system pupil. The method comprises a first step of producing at least one irradiating light beam with an irradiating optical system for irradiating an object and projecting the at least one irradiating light beam to a first portion of the system pupil. The method also comprises a second step of reflecting the at least one irradiating light beam at the first portion of the system pupil with a first surface of a two-sided rotatable mirror to the object. The first and second steps together define an irradiation path for the at least one irradiating light beam.

The method further comprises a third step of reflecting the at least one irradiating light beam from the object as at least one detecting light beam to a second surface of the two-sided rotatable mirror, and reflecting the at least one detecting light beam from the second surface of the two-sided rotatable mirror to a photodetector. In addition, the method comprises a fourth step of redirecting one of the at least one irradiating light beam and the at least one detecting light beam.

The method also comprises a fifth step of positioning the irradiating optical system and the photodetector so that one of the following two sequences of steps occurs. The first sequence of steps comprises reflecting the at least one irradiating light beam with the first surface of the two-sided rotatable mirror, and redirecting the reflected at least one irradiating light beam, reflected by the first surface of the two-sided rotatable mirror, through a second portion of the system pupil not covered by the two-sided rotatable mirror to the object. The second sequence comprises projecting the at least one detecting light beam reflected by the object through the second portion of the system pupil not covered by the two-sided rotatable mirror, redirecting the at least one detecting light beam having passed through the second portion of the system pupil to the second surface of the two-sided rotatable mirror, and reflecting the at least one detecting light beam from the second surface of the two-sided rotatable mirror to the photodetector.

The method also comprises a sixth step of steering both the at least one irradiating light beam and the at least one detecting light beam through the same angle when the at least one irradiating light beam is reflected by the first surface of the two-sided rotatable mirror and when the at least one detecting light beam is reflected by the second surface of the two-sided rotatable mirror.

The third step defines an observation path for the at least one detecting light beam. In addition, in order to prevent cross-talk between the at least one irradiating light beam and the at least one detecting light beam, all of the steps of the method are performed so that the irradiation path and the observation path are spaced from each other at least at the system pupil.

According to another aspect, the present invention which achieves one or more of these objectives relates to a beam steering optical system having a system pupil. The system comprises an irradiating optical system, a two-sided mirror, an objective lens, and a photodetector. The irradiating optical system produces at least one irradiating light beam for irradiating an object. The two-sided mirror is positioned to cover only a first portion of the system pupil. The two-sided mirror is also positioned to reflect with a first surface the at least one irradiating light beam received from the irradiating optical system and to reflect with a second surface at least one detecting light beam comprising the at least one irradiating light beam reflected from the object. The objective lens is positioned to receive the at least one irradiating light beam reflected from the first surface of the two-sided mirror and to focus the at least one irradiating light beam on the object.

The irradiating optical system, the two-sided mirror, and the objective lens together define an irradiation path for the at least one irradiating light beam. In addition, the photodetector is positioned to receive at least one detecting light beam reflected by the second surface of the two-sided mirror. Also, the objective lens, the two-sided mirror, and the photodetector together define an observation path for the at least one detecting light beam. Moreover, one of the irradiation path and the observation path intersects the first portion of the system pupil and the other one of the irradiation path and the observation passes through a second portion of the system pupil not covered by the two-sided mirror. In addition, to prevent cross-talk between the at least one irradiating light beam and the at least one detecting beam the irradiation path and the observation path are spaced from each other at least at the system pupil.

These and other features and advantages of the present invention will be more readily understood upon reviewing the following detailed description of preferred embodiments taken in conjunction with the attached drawings.

DETAILED DESCRIPTION OF PREFERRED EMBODIMENTS

Figure 1A:
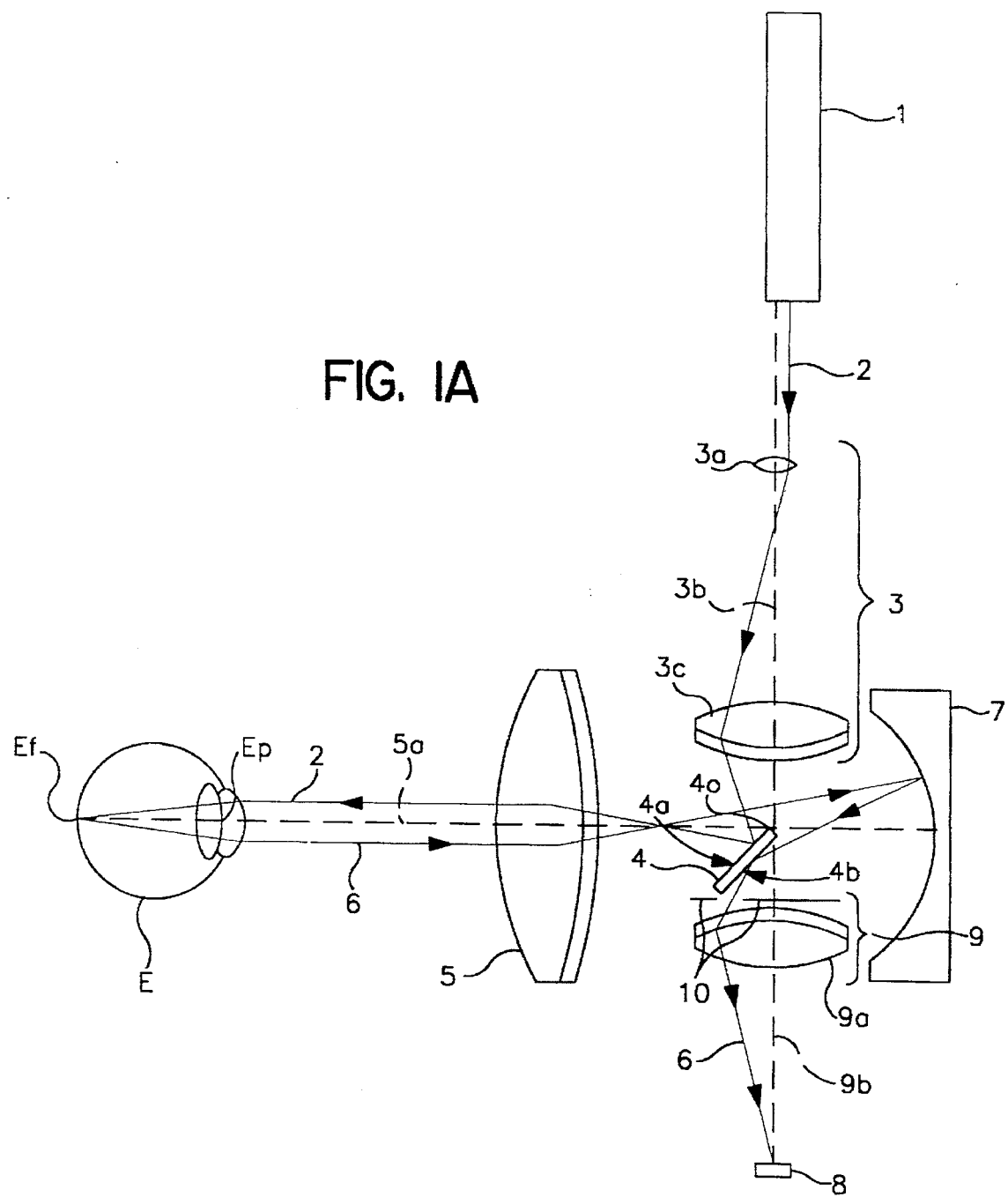
FIG. 1A is a schematic view of a first embodiment of the present invention.

A first embodiment of the present invention is the one-dimensional steering optical system shown in FIG. 1A. The system includes an irradiating optical system comprising a laser source 1, which emits an irradiating beam 2 irradiating an object such as the fundus Ef of an eye E of an examinee. This is accomplished by first passing the irradiating beam 2 through a lens 3a of the irradiating optical system 3 positioned in front of the laser source 1. The irradiating beam 2 is incident on the lens 3a at a position spaced from the optical axis 3b thereof. The lens 3a directs the irradiating beam 2 to cross the optical axis 3b along an irradiating path to a lens 3c of the irradiating optical system. The irradiating beam 2 is incident on the lens 3c at a position spaced from the optical axis thereof, which is also the axis 3b. As a result, the optical axis 3b is the optical axis of the irradiating optical system. The irradiating optical system 3 directs the irradiating beam 2 onto a first (front) surface 4a of a two-sided rotatable mirror 4. The first surface 4a of the two-sided rotatable mirror 4 reflects the irradiating beam 2 to an objective lens 5 facing the examinee's eye E at a point spaced from and above the optical axis 5a thereof. The objective lens 5 directs the irradiating beam 2 onto the fundus Ef of the eye E.

The two-sided rotatable mirror 4 is located at and covers only a portion of the system pupil. The system pupil is located on a plane perpendicular to the optical axis 5a of the objective lens 5 around the point at which this plane crosses the optical axis 3b of the irradiation optical system. The two-sided rotatable mirror 4 pivots and steers the irradiating beam 2 about an axis 4o, which is perpendicular to the optical axis 3b of the irradiating optical system on this plane.

The axis 4o also extends along the edge of the mirror 4 closest to the lens 3c of the irradiating optical system. This edge is positioned at the intersection of the optical axis 5a of the objective lens 5 and the optical axis 3b of the irradiating optical system. Alternatively, the axis 4o can extend along other lines perpendicular to the optical axis 3b of the irradiating optical system and the edge can be spaced from the intersection of the axes 5a and 3b. By such an arrangement, the two-sided rotatable mirror 4 covers only half of the system pupil. As a result, the irradiating beam 2 is incident on this half of the system pupil and is reflected by the first surface 4a, while a beam reflected from the eye E, passes through the other half of the system pupil and does not strike the first surface of the two-sided rotatable mirror 4, as will be discussed below.

The objective lens 5 is so positioned as to make the system pupil conjugate with the pupil Ep of the examinee's eye E. Consequently, the irradiating beam 2 travels through only one half of the pupil Ep of the examinee's eye E. As the two-sided rotatable mirror 4 rotates, the irradiating beam 2 is steered to irradiate, through the pupil Ep, one point on a particular line on the eye fundus Ef.

The light source 1, the lens 2, the lenses 3b and 3c of the irradiating optical system, the two-sided rotatable mirror 4, and the objective lens 5 together define an irradiation path for the irradiating beam 2 from the light source 1 to the eye E.

The light reflected by the point on the fundus Ef is called a detecting beam 6. The detecting beam 6 is directed close to but separated from the irradiating path followed by the irradiating beam 2 and in the reverse direction. Thus, the detecting beam 6 passes through the other half of the pupil Ep, travels below the optical axis 5a to the objective lens 5, and passes through the other half of the system pupil not covered by the two-sided rotatable mirror 4. This latter feature is accomplished by the eccentric location of the two-sided rotatable mirror 4 or its asymmetrical shape.

Figure 2:
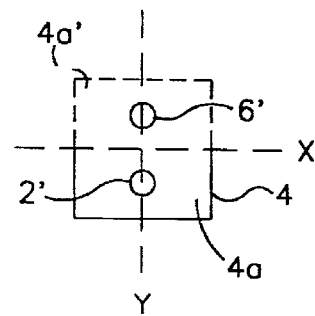
FIG. 2 is a schematic view of the system pupil of the embodiment shown in FIG. 1A when viewed from the objective lens 5.

FIG. 2 shows the system pupil of FIG. 1A when viewed from the objective lens 5. The system pupil appears as a square, the lower half of which is covered by the first surface 4a of the two-sided rotatable mirror 4. This is illustrated by the solid rectangle labelled 4a. The circle labelled 2' denotes the cross-section of the irradiating beam 2 which is reflected by the first surface 4a. The upper half of the system pupil is shown as a rectangle in dashed lines and is denoted by 4a'. The detecting beam 6 passes through the upper half 4a' of he system pupil. This is shown by the circle labelled 6', which denotes the cross-section of the detecting beam 6.

The detecting beam 6, after passing through the upper half 4a' of the system pupil, strikes a beam redirecting system for redirecting the detecting beam 6. In this embodiment the beam redirecting system comprises a curved relay mirror 7, which flips the detecting beam 6 and redirects it to the second surface 4b of the two-sided rotatable mirror 4. As the two-sided rotatable mirror 4 rotates, the second surface 4b performs a steering correction on the detecting beam 6, which is in the opposite direction to the steering operation performed by the first surface 4a on the irradiating beam 2, but of the same magnitude. This is accomplished because, as the two-sided rotatable mirror 4 rotates, it rotates the irradiating beam 2 and the detecting beam 6 through the same angle simultaneously.

The center of curvature of the curved relay mirror 7 is located at the center of the system pupil. Therefore, the second surface 4b of the two-sided rotatable mirror 4 is conjugate with the upper half 4a' of the system pupil at a magnification of −1. Moreover, as a result, the position of the detecting beam 6 on the second surface 4b and the position of the detecting beam 6 on the system pupil as indicated by 6' in FIG. 2 are symmetrically located with respect to the x axis shown in FIG. 2. In addition, the position of the detecting beam 6 on the second surface 4b is almost the same as the position of the irradiating beam 2 on the first surface 4a, which is indicated by 2' in FIG. 2, except that these two beams are reflected by different surfaces of the two-sided rotatable mirror 4.

The second surface 4b reflects the detecting beam 6 to a position-sensing photodetector 8 through a detecting optical system 9. The detecting optical system 9 comprises a lens 9a having an optical axis 9b, and an eccentric aperture 10. The eccentric aperture 10 is located between the two-sided rotatable mirror 4 and the lens 9a and is spaced from the optical axis 9b of the detecting optical system 9. From the second surface 4b, the detecting beam 6 passes through the eccentric aperture 10 and travels to the lens 9a off axis from axis 9b, which focuses the detecting beam 6 on the position-sensing photodetector 8.

Thus, the objective lens 5, the curved relay mirror 7, the two-sided rotatable mirror 4, the eccentric aperture 10, the lens 9a, and the position-sensing photodetector 8 define an observation path along which the detecting beam 6 is directed from the eye E to the position-sensing photodetector 8. As will be appreciated, because the observation path is spaced from the irradiation path at least at the system pupil, cross-talk is eliminated between the irradiating beam 2 and the detecting beam 6.

When the two-sided rotatable mirror 4 rotates, the irradiating beam 2 is directed to one point on a particular line of the eye fundus Ef as described above, and the detecting beam 6 reflected from such a point is always redirected to the position-sensing photodetector 8. As a result, the first embodiment is a one-dimensional beam steering optical system. Since the system pupil is divided into two halves, one for the irradiating beam 2 and the other for the detecting beam 6, the path of each beam is always separated in the anterior portion of the examinee's eye E, such as in the cornea, the anterior chamber, and the lens. This separation of the two light beams reduces cross-talk therebetween and is accomplished with a simple structure.

Figure 1B:
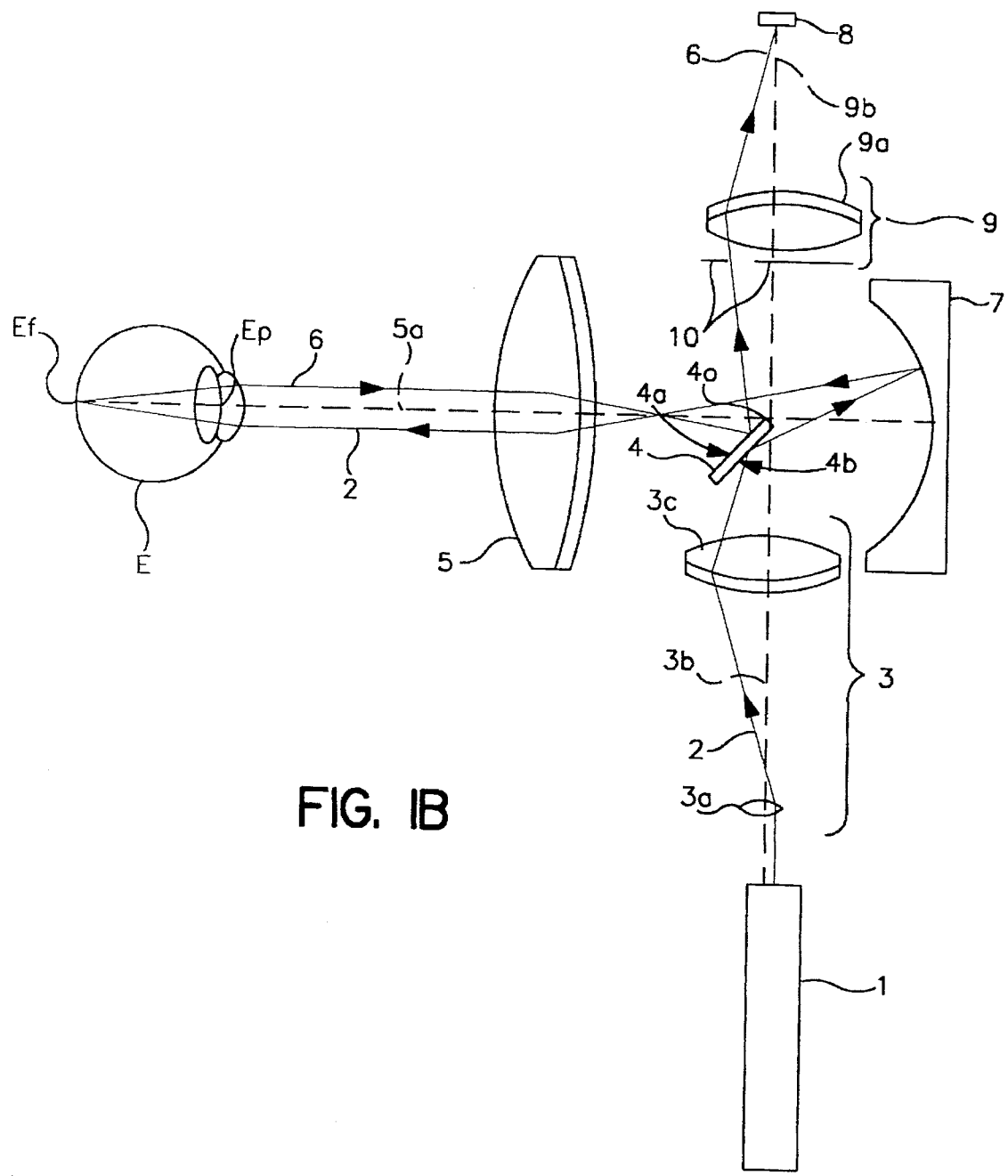
FIG. 1B is a schematic view of an alternative embodiment of the first embodiment of the present invention.

In an alternative embodiment shown in FIG. 1B, the laser source 1 and the position-sensing photodetector 8 are interchanged. In addition, compared with the FIG. 1A embodiment, the lens 9a and the aperture 10 are moved so that they are above the relay mirror 7 in front of the position-sensing photodetector 8, and the lenses 3a and 3c are moved so that they are below the relay mirror 7 in front of the laser source 1. Otherwise, this embodiment is identical to the embodiment shown in FIG. 1A. As a result, the irradiating light beam 2 passes through the lenses 3b and 3c and is reflected by the surface 4b, a first (front surface), of the two-sided rotatable mirror 4 to the curved relay mirror 7. The curved relay mirror 7 reflects the irradiating light beam 2 through the portion of the system pupil not covered by the mirror 4 to the objective lens 5, which directs the irradiating light beam 2 to the eye E. As a result, the eye E reflects the detecting beam 6 through the objective lens 5. The objective lens 5 directs the detecting beam 6 to the surface 4a, a second (rear) surface, of the mirror 4. The surface 4a of the mirror 4 reflects the detecting beam 6 through the aperture 10 and the lens 9a to the position-sensing photodetector 8.

In another alternative embodiment, the curved relay lens 7 can be replaced by cata-dioptric relay optics constructed of one curved or flat mirror and one or a plurality of coaxial elements coaxial with the optical axis of the objective lens 5 to reduce the aberration caused thereby, for wider angle beam steering or for a beam of a larger diameter. In this alternative embodiment, the cata-dioptric relay optics make one half of the system pupil conjugate with the second surface 4b of the two-sided rotatable mirror 4 at a magnification of almost or substantially −1.

A simple way to modify this system to accomplish two-dimensional beam steering is to make the two-sided rotatable mirror 4 rotatable like a gimbaled mirror, freely in any direction. Or, the two-sided rotatable mirror 4 can be rotatable about two perpendicular axes for steering the irradiating beam 2 and the detecting beam 6 in two dimensions because in this embodiment, the beam redirecting system is constructed to redirect the detecting beam 6 in two perpendicular planes.

As another alternative, an additional mirror, rotatable perpendicular to the direction in which the two-sided rotatable mirror 4 rotates, can be provided close to the two-sided rotatable mirror 4.

Figure 3:
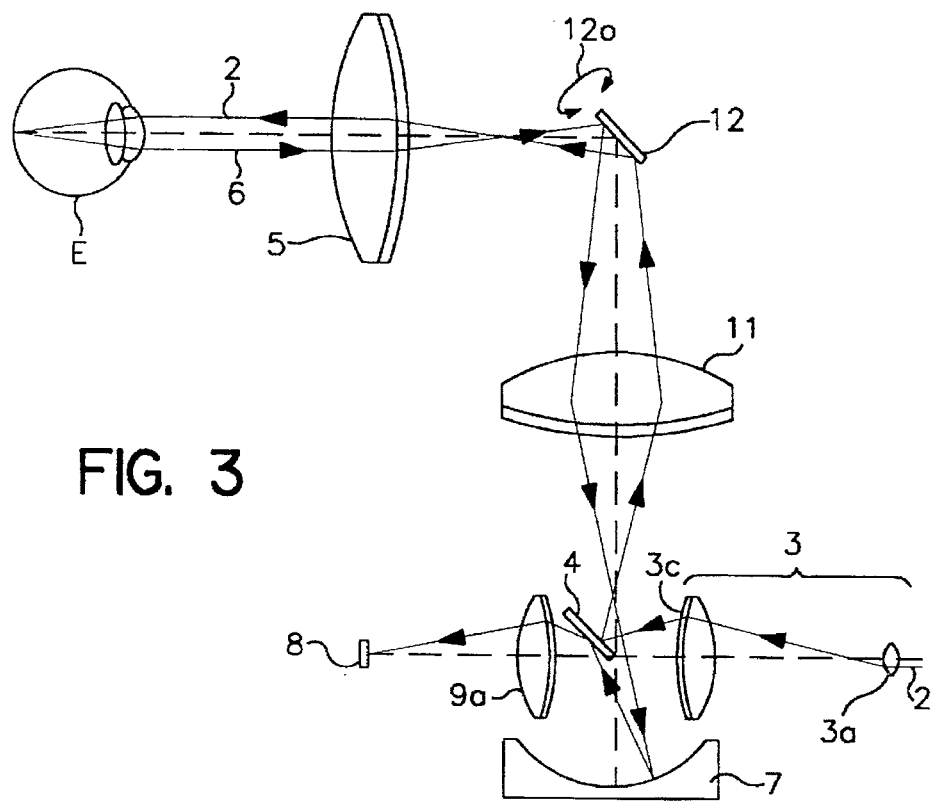
FIG. 3 is a schematic view of a second embodiment of the present invention.

A second embodiment of the present invention is shown in FIG. 3. In this embodiment, elements identified by the same reference numbers and letters used in FIGS. 1A and 2 denote the same or similar elements, and therefore, a detailed discussion thereof will be omitted.

In the second embodiment, a relay optical system comprising a relay lens 11 and a rotatable mirror 12 are provided between the two-sided rotatable mirror 4 and the objective lens 5. The relay lens 11 makes the rotatable mirror 12 conjugate with the system pupil at a magnification of −1. One surface of the rotatable mirror 12 reflects both the irradiating beam 2 and the detecting beam 6. Both beams 2 and 6 are steered by the rotatable mirror 12 about an axis 12o. The axis 12o can extend along any direction perpendicular to the axis 4o of the two-sided rotatable mirror 4. As the mirrors 4 and 12 rotate and steer the beams 2 and 6, they cause the irradiating beam 2 to scan the eye fundus Ef in two dimensions, like a raster scanning pattern.

Figure 4:
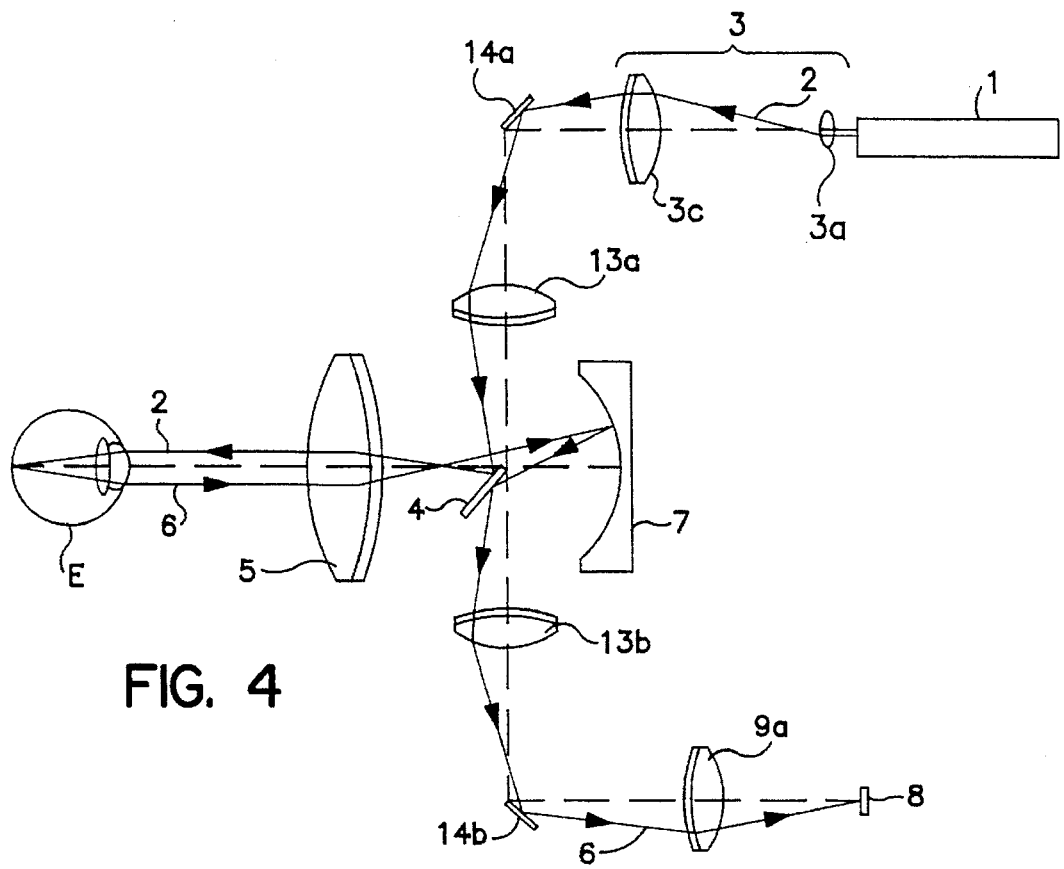
FIG. 4 is schematic view of a third embodiment of the present invention.

FIG. 4 shows a third embodiment of the present invention also illustrating a two-dimensional beam steering system. In this embodiment, elements identified by the same reference numbers and letters used in FIGS. 1A and 2 denote the same or similar elements, and therefore, a detailed discussion thereof will be omitted. This beam steering optical system comprises a pair of relay optical systems, one relay optical system comprising a relay lens 13a and the other relay optical system comprising a relay lens 13b. The beam steering optical system also comprises a pair of rotatable mirrors 14a and 14b. Relay lens 13a makes the system pupil conjugate with the rotatable mirror 14a, while relay lens 13b makes the system pupil conjugate with the rotatable mirror 14b. Relay lens 13b and mirror 14a are located in the irradiation path of the irradiating beam 2 between the lens 3c of the irradiating optical system and the two-sided rotatable mirror 4, while the relay lens 13b and the mirror 14b are located in the observation path of the detecting beam 6 between the two-sided rotatable mirror 4 and the detecting optical system 9 and the position-sensing photodetector 8. Mirrors 14a and 14b rotate about separate axes, each of which is perpendicular to axis 4o. The rotation axis of mirror 14a extends through the center of mirror 14a in the direction of the height thereof, while the rotation axis of mirror 14b extends through the center of mirror 14b in the direction of the height thereof. When mirrors 14a and 14b are driven to rotate simultaneously through the same angle about their respective axes, (accompanied by the rotation of the two-sided rotatable mirror 4), the irradiating beam 2 is scanned in two dimensions on the eye fundus Ef. As a result, this system acts as a two-dimensional beam steering system.

Unlike the second embodiment shown in FIG. 3 in which the mirror 12 reflects both the irradiating beam 2 and the detecting beam 6, mirror 14a reflects only the irradiating beam 2, while the mirror 14b reflects only the detecting beam 6. By using separate mirrors for reflecting the irradiating and detecting beams, cross-talk between the two beams is reduced even more than in the second embodiment. This two-dimensional beam steering system is useful in ophthalmic instruments like a scanning laser ophthalmoscope.

Figure 5:
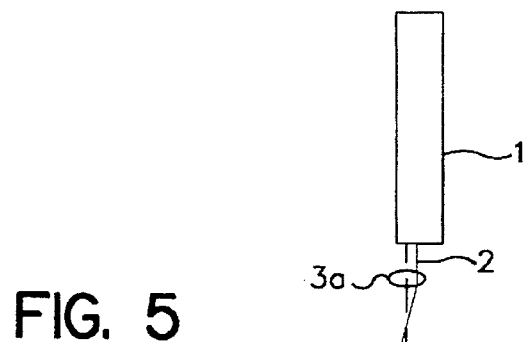
FIG. 5 is a schematic view of a fourth embodiment of the present invention.
Figure 5:
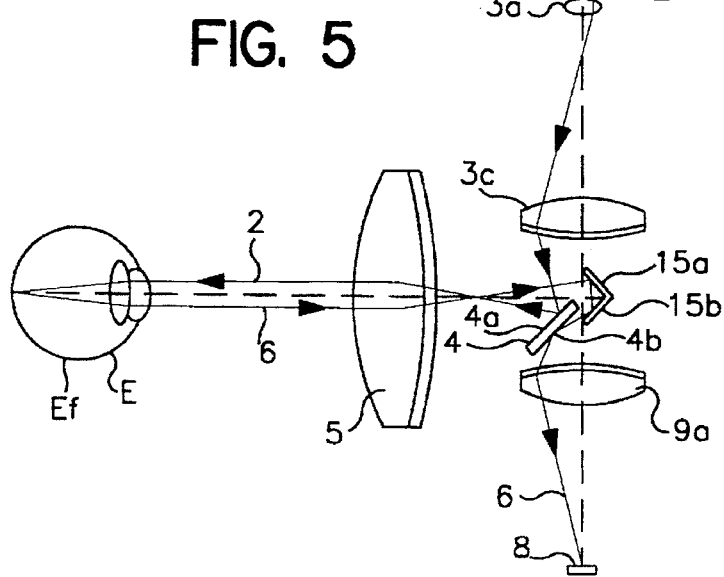

FIG. 5 shows a fourth embodiment in which the relay mirror 7 is replaced by a pair of small mirrors 15a and 15b forming a ninety degree angle therebetween and whose surfaces face each other. The two mirrors 15a and 15b intersect along an axis parallel to the rotation axis of the two-sided rotatable mirror 4. In this embodiment, elements identified by the same reference numbers used in FIGS. 1A and 2 denote the same or similar elements, and therefore, a detailed discussion thereof will be omitted. Mirrors 15a and 15b are located very close to and behind the two-sided rotatable mirror 4 on the opposite side thereof from the objective lens 5. When the detecting beam 6 passes through the uncovered portion of the system pupil, it is reflected by mirror 15a to mirror 15b. Mirror 15b, in turn, reflects the detecting beam 6 to the second surface 4b of the two-sided rotatable mirror 4. The reflection of the detecting beam 6 is performed by mirrors 15a and 15b in a plane perpendicular to the axis 4o of the two-sided rotatable mirror 4. Both relay mirror 7 used in the first, second, and third embodiments, and mirrors 15a and 15b act as beam redirecting means. Mirrors 15a and 15b, however, are simpler in construction.

One drawback of mirrors 15a and 15b is that since these mirrors redirect the detecting beam 6 in one dimension in one plane, the axis 4o of the two-sided rotatable mirror 4 must be perpendicular to this plane and cannot be replaced by a gimbaled mirror for two-dimensional steering. To overcome this disadvantage, mirrors 15a and 15b can be replaced by a three mirror system, the surfaces of which are perpendicular to each other, i.e. a corner cube. The three mirror system reflects the detecting beam 6 three times to redirect the detecting beam 6 from the objective lens 5 to the second surface 4b of the two-sided rotatable mirror 4. Thus, the detecting beam 6 is twice reflected in two perpendicular planes to exit the three mirrors parallel to the direction in which it entered.

Figure 6:
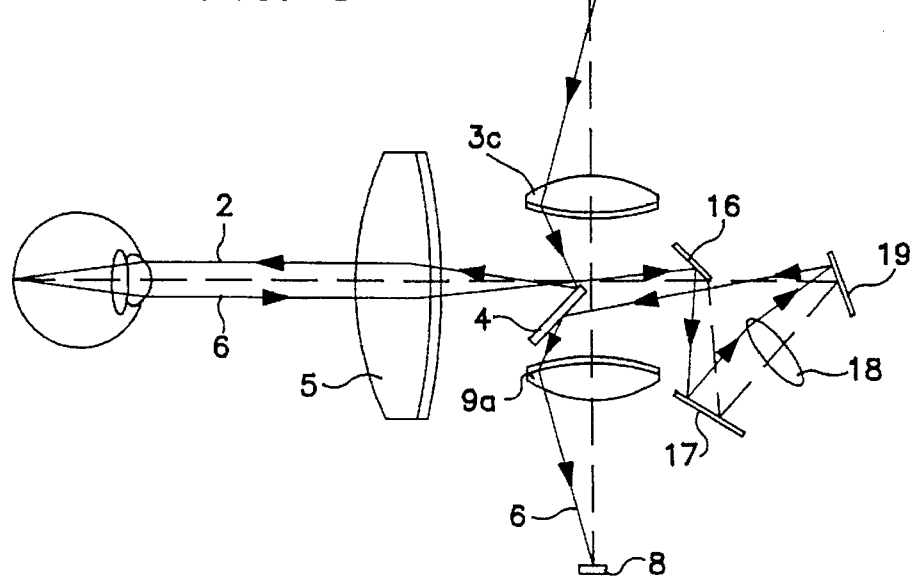
FIG. 6 is a schematic view of a fifth embodiment of the present invention.

A fifth embodiment of the present invention is shown in FIG. 6. Elements in FIG. 6 identified by the same reference numerals and letters used in FIGS. 1A and 2 denote the same or similar elements, and therefore, a detailed discussion thereof will be omitted. In this embodiment the relay mirror 7 is replaced by three mirrors, the normals of which are not coaxial with the optical axis 5a of the objective lens 5, and a relay lens. More specifically, FIG. 6 shows the detecting beam 6 passing through the uncovered portion of the system pupil to a mirror 16. The detecting beam 6 is reflected by mirror 16 to a mirror 17, which reflects it through a relay lens 18, after which the detecting beam 6 is incident on a mirror 19, reflecting the detecting beam 6 to the second surface 4b of the two-sided rotatable mirror 4. The relay lens 18 makes the uncovered portion of the system pupil conjugate with the second surface 4b of the two-sided rotatable mirror 4.

In all of the embodiments described above, the directions in which the irradiating beam 2 and the detecting beam 6 travel can be reversed and the invention will function in the same way. This can be accomplished by interchanging the laser source 1 and the position-sensing photodetector 8, as shown in FIG. 1B. Furthermore, eccentric beam positioning is performed for only the beam redirected by the beam redirecting means. If one of the beams reflected by the first surface or the second surface of the two-sided rotatable mirror 4 travels along the optical axis 5a itself of the objective lens 5, the two-sided rotatable mirror 4 should cover the portion of the system pupil on the axis 5a.

Figure 7A:
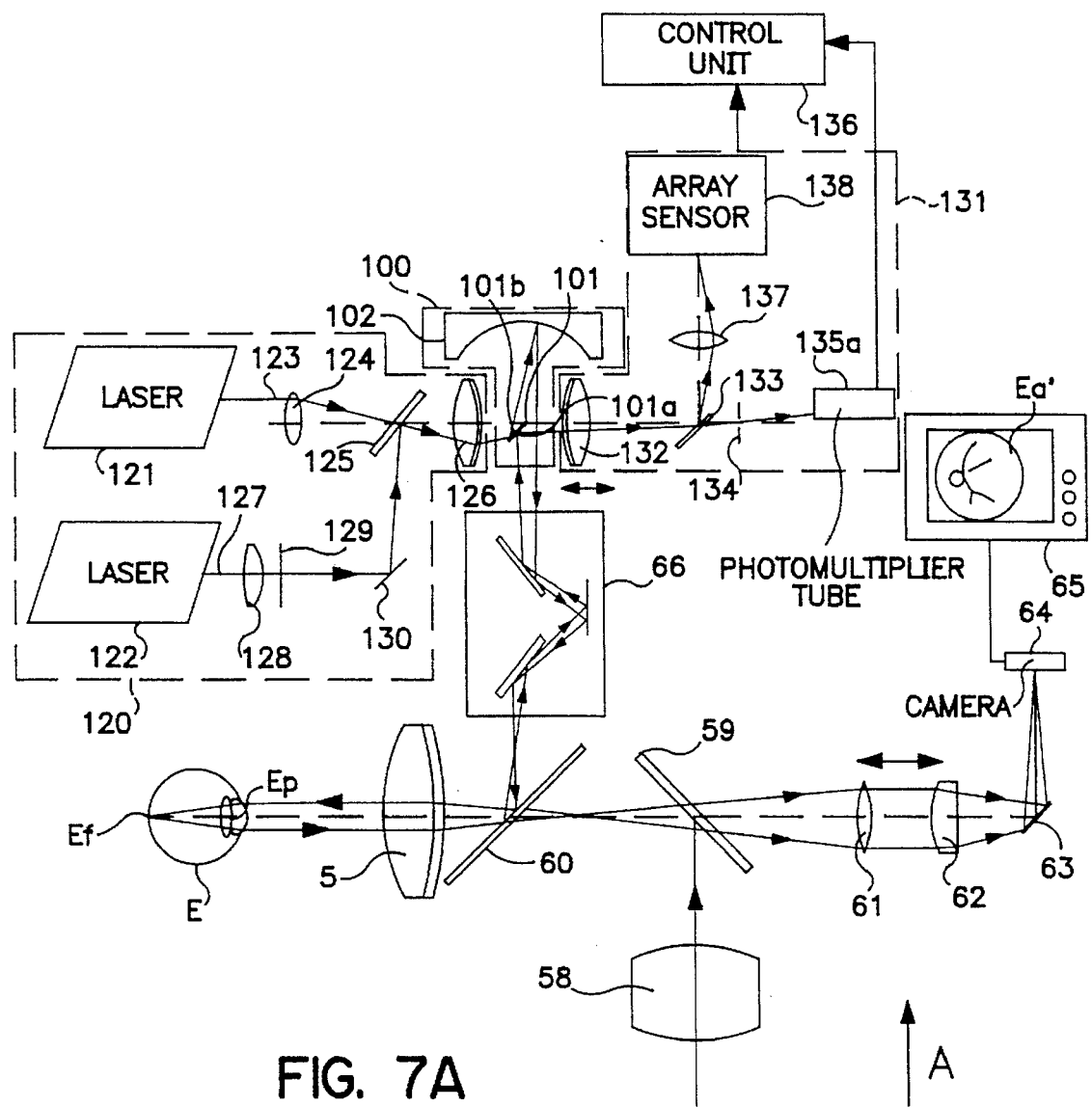
FIG. 7A is a schematic side view of a sixth embodiment of the present invention.
Figure 7B:
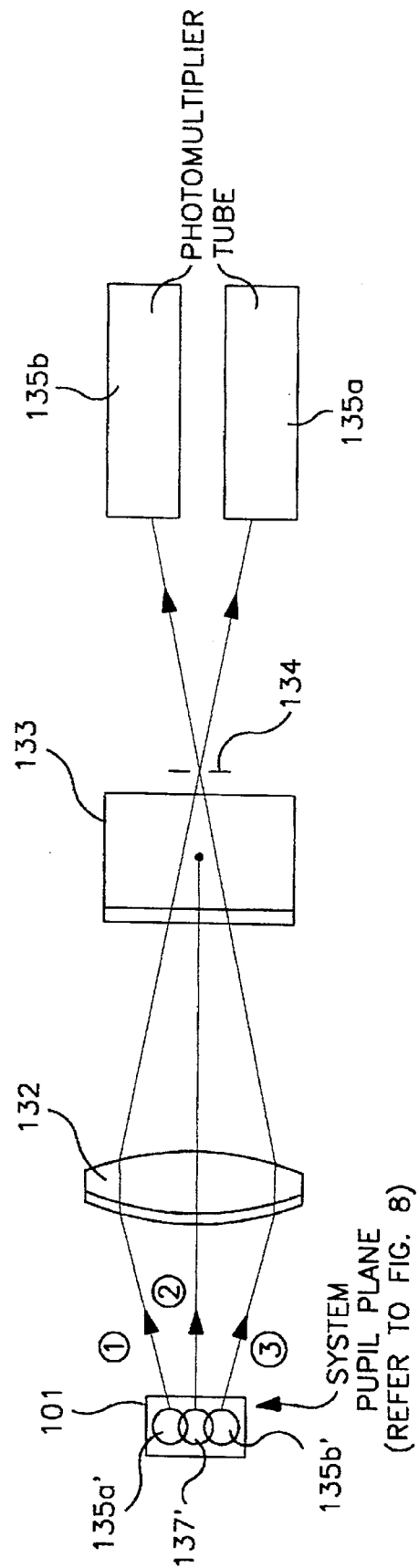
FIG. 7B is a schematic bottom view of the apparatus shown in FIG. 7A in the direction A.

FIGS. 7A and 7B illustrate a sixth embodiment of the present invention which is a laser Doppler velocimeter for measuring the blood flow in a retinal vessel of an examinee's eye E. In a velocimeter, as disclosed, for example, in U.S. Pat. No. 5,106,184, a laser beam is projected onto the retinal vessel of an examinee's eye E to determine the velocity of blood flow therein. A Doppler signal is obtained from heterodyne detection of light reflected from moving red blood cells in the retinal vessel and reference light reflected by the retinal vessel wall. Whenever eye movement occurs, the laser beam must be held on the retinal vessel to obtain a reading, but it need not be held at the same position in the direction of the axis of the vessel, because the Doppler signal, determined from the velocity difference between the red blood cells and the retinal vessel wall, is not affected by eye movements in that direction. Therefore, it is sufficient to use a one-dimensional beam steering system, as shown in FIGS. 7A and 7B.

Elements in FIGS. 7A and 7B identified by the same reference numerals and letters used in FIGS. 1A and 2 denote the same or similar elements, and therefore, a detailed discussion thereof will be omitted. The velocimeter shown in FIG. 7A has a one-dimensional eye tracking system using a beam steering optical system 100 according to the present invention. The velocimeter also comprises an illumination light source 51, such as a tungsten lamp emitting white light, for illuminating the eye E. In order to move the light along an optical path from the illumination light source 51 to the eye E the following elements are provided therebetween: a band-pass filter 52 transmitting only yellow light therethrough, a condenser lens 53 for condensing the yellow light transmitted through the band-pass filter 52 onto a mirror 54, a field lens 55 receiving the light reflected by the mirror 54 and transmitting it through a ring slit 56 to relay lenses 57 and 58 and then to an apertured mirror 59, which reflects the light to a band-pass mirror 60. The light is transmitted through the band-pass mirror 60 to the objective lens 5, which focuses the light onto the eye fundus Ef.

More specifically, the objective lens 5 faces the examinee's eye E and focuses the yellow ring-slit image of the ring slit 56 on the pupil Ep of the eye E and directs a uniform yellow light to the entire fundus Ef of the eye E. This yellow light is reflected by the fundus Ef, and returns along the same path as the illuminating light through the objective lens 5 and the band-pass mirror 60, to the apertured mirror 59. The reflected yellow light from the fundus Ef travels through the aperture in the apertured mirror 59 to a retinal observation system. The retinal observation system comprises a focusing lens 61, an imaging lens 62, a mirror 63, a CCD (charge coupled device) black and white camera 64, and a TV monitor 65. The reflected yellow light passing through the aperture of the apertured mirror 59 is focused by the focusing lens 61 and imaged by the imaging lens 62 onto the CCD camera 64 after being reflected by the mirror 63. The yellow retinal image of the eye fundus Ef is converted by the CCD camera 64 to a TV signal, which is fed to the TV monitor 65, which, in turn, displays a retinal image Ea'. This system enables the examiner to operate the velocimeter while observing the retinal image on the TV monitor 65.

The velocimeter also includes an image rotator 66 located between the band-pass mirror 60 and the beam steering optical system 100. The image rotator 66 is positioned to reflect light to the band-pass mirror 60 and to receive light from the eye E, having passed through the objective lens 5 and having been reflected by the band-pass mirror 60. Thus, the image rotator 66 is positioned in an optical path branching off from the band-pass mirror 60. The image rotator 66 comprises three mirrors which are so positioned to reflect light received from the band-pass mirror 60 to the beam steering optical system 100 and to reflect light received from the beam steering optical system 100 to the band-pass mirror 60.

The velocimeter also includes an irradiating optical system 120 located on one side of the beam steering optical system 100 and a detecting optical system 131 located on the other side of the beam steering optical system 100.

The beam steering optical system 100 comprises a two-sided rotatable mirror 101 and a curved mirror 102. These components are constructed and operate in a similar manner to the two-sided rotatable mirror 4 and the mirror 7 shown in FIG. 1B. As in the previous embodiments, half of the pupil of the beam steering optical system 100 is covered by the two-sided rotatable mirror 101. In addition, the system pupil is conjugate with the pupil Ep of the examinee's eye E. The two-sided rotatable mirror 101 has a first surface 101b (nearer to the light source, e.g. lasers 121 and 122) and a second surface 101a (nearer to the detecting optical system 131), whose operation will be discussed below.

The irradiating optical system 120 comprises a laser 121 for velocity measurement and a laser 122 for tracking control. The laser 121 emits a red laser beam 123 which is projected through a lens 124 along a path spaced from the optical axis of the lens 124. The lens 124 focuses the red laser beam 123 at a point on the optical axis thereof conjugate with the fundus Ef of the examinee's eye E in front of a dichroic mirror 125. The red laser beam then passes through the dichroic mirror 125 to a lens 126 provided on the other side of the dichroic mirror 125 for directing light to the beam steering optical system 100 as will be discussed in more detail below. The laser 122 emits a green laser beam 127 toward a cylindrical lens 128 and an aperture 129. The green laser beam 127 is formed into a stripe shape as a result of passing through the cylindrical lens 128 and the aperture 129. After passing through the aperture 129, the green laser beam 127 strikes a mirror 130, and is reflected to the rear surface of the dichroic mirror 125. The dichroic mirror 125 combines the red laser beam 123 transmitted therethrough and the green laser beam 127 reflected therefrom into a single combined laser beam, which is directed to the beam steering optical system 100 through the lens 126.

From the beam steering optical system 100, the single combined laser beam (called the irradiating beam when travelling from the irradiating optical system 120 to the eye E and called the detecting beam when travelling from the eye to and through the detecting optical system 131) is reflected by the first surface 101b of the two-sided rotatable mirror 101 to the curved mirror 102. The curved mirror 102 reflects the irradiating beam through the half of the system pupil not covered by the two-sided rotatable mirror 101 to the image rotator 66. The image rotator 66 reflects the irradiating beam to the mirror 60 which reflects the irradiating beam through the objective lens 5 to the eye fundus Ef.

Thus, the irradiating optical system 120, the beam steering optical system 100, the image rotator 66, the mirror 60, and the objective lens 5 together define an irradiation path for the irradiating beam.

The eye fundus Ef reflects the irradiating beam, which is called a detecting beam once it is reflected by the eye fundus Ef. The detecting beam travels along an optical path close to but separated from the optical path travelled by the irradiating beam. Thus, the detecting beam 1) is reflected by the eye fundus Ef through a different part of the pupil Ep than the irradiating beam, 2) travels along a different path to and through the objective lens 5, and 3) travels along a different path from the objective lens 5 to the mirror 60, to the image rotator 66, and to the second surface 101a of the two-sided rotatable mirror 101, where the detecting beam is reflected to the detecting optical system 131. At the same time, the dichroic mirror 60 transmits a small amount, less than 10%, of the green portion of the single combined laser beam to the camera 64, through the apertured mirror 59, the focusing lens 61, and the imaging lens 62 and by reflection from the mirror 63. The two edges of this beam are shown by two arrows leaving mirror 59 and passing through lenses 61 and 62. As a result, the person examining the examinee's eye can view the position of the single combined laser beam on the image of the eye fundus Ef on the TV monitor 65.

After entering the detecting optical system 131, the single combined laser beam is focused by a focusing lens 132 and strikes a dichroic mirror 133. The dichroic mirror 133 separates the red and green laser beams, as will now be described. The dichroic mirror 133 transmits the red laser beam 123, which is focused on a confocal aperture 134, conjugate with the eye fundus Ef. From the aperture 134, the red laser beam 123 is projected onto two photomultiplier tubes 135a, 135b located at positions conjugate with the eye pupil Ep. Although FIG. 7A shows only photomultiplier tube 135a, another photomultiplier tube 135b is positioned behind tube 135a, as shown in FIG. 7B. Moreover, although the side view of FIG. 7A shows only one light beam leaving lens 132, in fact there are three light beams leaving lens 132, as shown in the bottom view of FIG. 7B. These three light beams are three detecting light beams ①②③ reflected by the surface 101b at the system pupil plane. Red laser beam 123 comprises the light beams ① and ③ since the incident plane of the photomultiplier tubes 135a and 135b is conjugate with the system pupil plane and the beams pass through the mirror 133 and the aperture 134. These three detecting light beams correspond to images 135a', 137', and 135b' shown in FIG. 8. Both red laser detecting light beams ① and ③ pass through the lens 132 and the dichroic mirror 133, and the aperture 134. Then, red laser detecting light beam ① enters photomultiplier tube 135b and red laser detecting light beam ③ enters photomultiplier tube 135a. By using two photomultiplier tubes 135a, 135b, signals from red blood cells in the retinal vessel of the eye E and signals from the retinal vessel wall are detected in two directions, thereby permitting a Doppler signal indicative of the velocity of blood flow to be determined by a system control unit 136 which receives the output from the photomultiplier tubes 135a, 135b.

The green laser beam 127, which is denoted by ② after being reflected by the surface 101b of the mirror 101, passes through lens 132, is reflected by the dichroic mirror 133, through a lens 137, to an array sensor 138 located at a position conjugate with the eye fundus Ef, the image of which is at a higher magnification than at the camera 64. In this embodiment, the array sensor 138 is equivalent to the position-sensing photodetector 8 in FIGS. 1–6. The output of the array sensor 138 is transmitted to the control unit 136. The control unit 136 generates data indicative of the movement of the retinal vessel of the eye E from the output of the sensor 138. This data is used by the control unit 136 to control an actuator-like galvanometer (not shown) which rotates the two-sided rotatable mirror 101 in the beam steering optical system 100, so that the movement of the retinal vessel in one dimension is compensated for by the rotation of the two-sided rotatable mirror 101 to keep the red and green laser beams on the retinal vessel to be measured.

Figure 8:
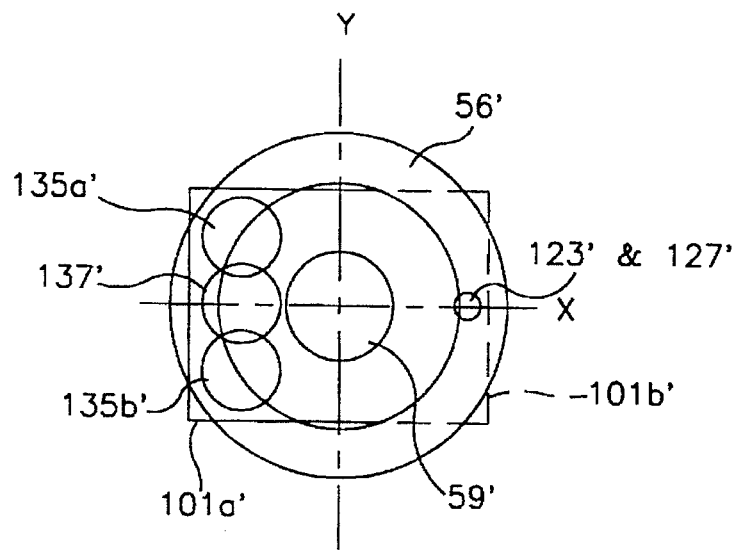
FIG. 8 is a schematic view of images 56', 59', 101a', 101b', 123', 127', 135a', 135b', and 137' on the eye pupil Ep.

Thus, the objective lens 5, the mirror 60, the image rotator 66, the two-sided rotatable mirror 101, and the detecting optical system 131 together comprise an observation path for the detecting beam. The elements defining the irradiation path and the elements defining the observation path are so positioned and constructed to space the observation path from the irradiation path. The ring slit 56, the apertured mirror 59, the second surface 101a and the first surface 101b of the two-sided rotatable mirror 101, the photo-multiplier tubes 135a, 135b, and the lens 137 are located at positions conjugate with the pupil Ep of the examinee's eye E. Thus, the images 56', 59', 101a', 101b', 135a', 135b', and 137' of the ring slit 56, the apertured mirror 59, the second surface 101a and the first surface 101b of the two-sided rotatable mirror 101, the photo-multiplier tubes 135a, 135b, and the lens 137, respectively, are located on the pupil Ep of the eye E in the manner shown in FIG. 8. In this figure the images of the red and green laser beams at the pupil Ep are respectively denoted as 123' and 127' and are positioned on the X axis. As can be seen in FIG. 8, the images 101a' and 101b' of the first and second surfaces of the two-sided rotatable mirror 101 are located on opposite sides of the pupil. The rotation axis of the two-sided rotatable mirror 101 is the Y axis as seen at the pupil, and as shown in FIG. 8. As a result, the red and green laser beams will scan the eye fundus Ef along the X axis shown in FIG. 8. The longitudinal axis of the array sensor 138 extends along the X axis, as does the longitudinal axis of the stripe shaped green laser beam 127, to detect the retinal vessel location along the X axis. Before measurement, the image rotator 66 rotates to rotate the arrangement of images 101a', 101b', 123', 127', 135a', 135b', and 137' so that the Y axis coincides with the direction of the retinal vessel axis.

Figure 9:
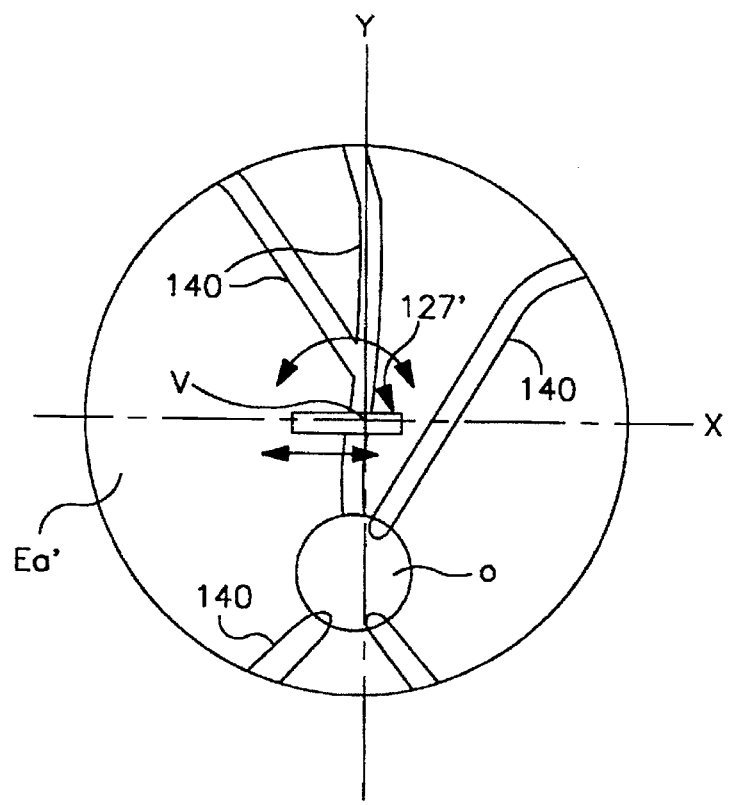
FIG. 9 is a schematic view of a fundus image displayed on a TV monitor 65.

FIG. 9 shows the retinal image Ea' displayed on the TV monitor 65. This figure shows blood vessels 140 of the eye fundus Ef and the optic nerve head o. In addition, FIG. 9 shows the stripe shaped image of the green laser beam 127' extending along the X axis to illuminate the position V to be measured only along the X axis. The examiner rotates the green laser beam 127 perpendicular to the retinal vessel to be measured by rotating the image rotator (by means not shown) and next, rotating the two-sided rotatable mirror 101 to steer the green laser beam 127 in the X direction. The array sensor 138 senses an image of this region in order to measure the position of V on the X axis. As a result, the control unit 136 produces a signal indicating the displacement of V from an initial or predetermined position to compensate for this displacement.

When the examiner depresses a measuring switch (not shown) to start measurements of the retinal vessel, the system control unit 136 receives a starting signal from the measuring switch, actuates the velocimeter to begin tracking of the blood vessels of the eye fundus Ef, and measures the velocity of the blood flow in the blood vessels of the retinal vessel. While the rotation angle of the two-sided rotatable mirror 101 is controlled by the control unit 136 to keep the red and green laser beams 123 and 127 on the target retinal vessel, the system control unit 136 also analyzes signals from the photo-multiplier tubes 135a and 135b using a Fast Fourier Transform technique to calculate the blood flow velocity.

Figure 10:
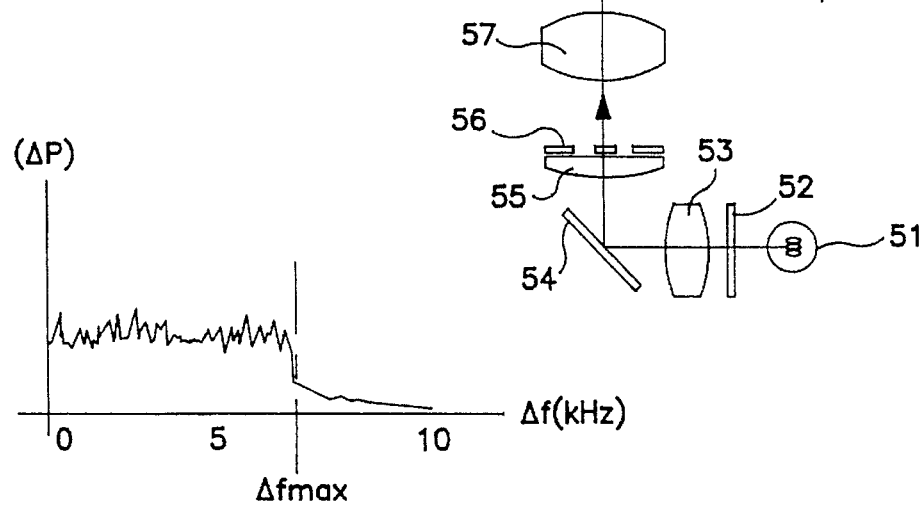
FIG. 10 is a graph of the result of a frequency analysis of a signal detected by one of the photomultiplier tubes 135a, 135b.

FIG. 10 shows a graph of the results of a frequency analysis by the system control unit 136 of a signal detected by one of the photo-multiplier tubes 135a, 135b. In this graph the abscissa represents a frequency change $\Delta f$ and the ordinate represents the power $\Delta p$ thereof. The relationship between the maximum shift in frequency $\Delta f_{max}$, the wave number vector $k_i$ of the red laser beam 123 as it leaves the laser 121, the wave number vector $k_s$ of the red laser beam 123 detected by one of the photo-multiplier tubes 135a, 135b, and the velocity vector $V_{max}$ of the maximum blood flow velocity can be expressed as:

$$\Delta f_{max} = (k_s - k_i) V_{max}.$$

In this embodiment the red laser beam 123 is detected by each of the photo-multiplier tubes 135a, 135b, which generates signals representative thereof. As a result, one can obtain:

$$|V_{max}| = (\lambda/n\alpha) \cdot |\Delta f_{max1} - \Delta f_{max2}|/\cos \beta$$

where $\lambda$ is the wavelength of the laser beam, n is the refractive index of the measured region of the eye E, $\alpha$ is the angle between the wave number vectors of the detected beams detected by the photo-multiplier tubes 135a, 135b, $\Delta f_{max1}$ is the maximum frequency shift of the signal detected by one of the photo-multiplier tubes 135a, 135b, $\Delta f_{max2}$ is the maximum frequency shift of the signal detected by the other of the photo-multiplier tubes 135a, 135b, and $\beta$ is the angle of a plane made by the wave number vectors of the beams detected by the photo-multiplier tubes 135a, 135b and $V_{max}$ (such as the direction of the axis of the blood vessel). It should be noted that the image rotator 66 can be adjusted so that $\beta=0$, as previously described. If this is done, it becomes unnecessary to measure the angle $\beta$; thus the system is simplified. In addition, when $\beta$ is 0 and the array sensor 138 for detecting the displacement of the retinal vessel is disposed perpendicular to the retinal vessel image, it becomes unnecessary to use a two dimensional tracking system.

As described above, when the arrangement of images on the pupil Ep is fixed as shown in FIG. 8, these parameters can be calculated using the axial length of the examinee's eye E, as is known to those skilled in the art.

By the arrangement shown in FIGS. 7A and 7B, the velocity of the blood flow in the retinal vessel can be determined with the Doppler velocimeter of the present invention with little or no noise or cross-talk between the beams irradiating the eye E (the incident beams) and the beams reflected by the eye E (the detecting beams) even if the eye moves during the measurement operations. Moreover, by using only one rotatable mirror at the pupil of a one-dimensional beam steering optical system and by having no point at which the incident beam path and the detecting beam path cross in the optical path between the light source and the system pupil and in the optical path between the photodetector and the system pupil, the arrangement of beams and apertures around the system pupil is optimized and simplified. As a result, the velocimeter shown in FIGS. 7A and 7B can be made compact and of a simple structure, like a conventional fundus cameras.

In a preferred embodiment, the following elements are comprised by the following specific components:

the red laser 121 can comprise the red laser diode by Hitachi, model no. HL6713G;

the green laser 122 can comprise a green He-Ne laser by Melles Griot, model no. 05LGR025-1;

the array sensor 138 can comprise the linear image sensor by Hamamatsu Photonics, model no. S3924-512F with an image intensifier attached thereto which is manufactured by Delft Instruments, model no. XX1450ED;

the photomultiplier tubes 135a and 135b can comprise photomultiplier tubes by Hamamatsu Photonics, model no. H5783-01;

the actuator of the two-sided rotatable mirrors can comprise a Galvano Meter Scanner; and the CCD camera 64 can comprise a Sony camera, model no. CCB-M25.

While the present invention has been described with respect to what is presently considered to be its preferred embodiments, it is understood that the invention in not limited to the disclosed embodiments, but is intended to cover various modifications and equivalent arrangements within the spirit and scope of the claims.

What is claimed is:

1. A beam steering optical system having a system pupil, said system comprising:

an irradiating optical system producing at least one irradiating light beam for irradiating an object;

a two-sided rotatable mirror positioned to cover only a first portion of the system pupil and to reflect with a first surface the at least one irradiating light beam received from said irradiating optical system;

an objective lens positioned to receive the at least one irradiating light beam reflected from said two-sided rotatable mirror and to focus the at least one irradiating light beam on the object, wherein said irradiating optical system, said two-sided rotatable mirror, and said objective lens together define an irradiation path for the at least one irradiating light beam;

a photodetector receiving at least one detecting light beam comprising the at least one irradiating light beam reflected by the object and then by a second surface of said two-sided rotatable mirror; and beam redirecting means for redirecting one of the at least one irradiating light beam and the at least one detecting light beam, wherein said irradiating optical system and said photodetector are positioned so that one of the following occurs:

the at least one irradiating light beam is reflected by the first surface of said two-sided rotatable mirror to said beam redirecting means which redirects the at least one irradiating light beam through a second portion of the system pupil not covered by said two-sided rotatable mirror and then through said objective lens to the object; and the at least one detecting light beam reflected by the object passes through the second portion of the system pupil not covered by said two-sided rotatable mirror to said beam redirecting means, and is redirected by said beam redirecting means to the second surface of said two-sided rotatable mirror which reflects the at least one detecting light beam to said photodetector;

wherein said two-sided rotatable mirror steers both the at least one irradiating light beam and the at least one detecting light beam through the same angle when said two-sided rotatable mirror rotates, wherein said objective lens, said two-sided rotatable mirror, and said photodetector together define an observation path for the at least one detecting light beam, and wherein the irradiation path and the observation path are spaced from each other at least at the system pupil.

2. The system defined by claim 1, wherein said objective lens receives the at least one detecting light beam reflected by the object and directs the at least one detecting light beam to the second portion of the system pupil not covered by said two-sided rotatable mirror, and wherein said beam redirecting means is positioned to receive the at least one detecting light beam after passing through the second portion of the system pupil, and redirects the at least one detecting light beam to the second surface of said two-sided rotatable mirror, said second surface of said two-sided rotatable mirror reflecting the at least one detecting light beam to said photodetector, wherein said objective lens, said two-sided rotatable mirror, said beam redirecting element, and said photodetector together define the observation path for the at least one detecting light beam.

3. The system defined by claim 1, wherein said beam redirecting means is positioned to receive the at least one irradiating light beam after being reflected by said first surface of said two-sided rotatable mirror and redirects the at least one irradiating light beam through the second portion of the system pupil to said objective lens, and wherein said irradiating optical system, said objective lens, said two-sided rotatable mirror, and said beam redirecting element together define the irradiation path for the at least one irradiating light beam.

4. The system defined by claim 1, wherein said beam redirecting means comprises two mirrors extending to form a ninety degree angle therebetween and having surfaces facing each other, wherein the two mirrors intersect along an axis parallel to the rotation axis of said two-sided rotatable mirror.

5. The system defined by claim 1, wherein said beam redirecting means comprises at least a curved or flat mirror coaxial with the optical axis of said objective lens, making the system pupil conjugate with the second surface of said two-sided rotatable mirror at a magnification of substantially −1.

6. The system defined by claim 1, wherein said two-sided rotatable mirror is rotatable around two perpendicular axes for steering the at least one irradiating light beam and the at least one detecting light beam two-dimensionally, wherein said beam redirecting means is constructed to redirect the at least one detecting light beam in two perpendicular planes corresponding to the rotating direction of said two-sided rotatable mirror.

7. The system defined by claim 1, further comprising a second rotatable mirror for steering the at least one irradiating light beam and the at least one detecting light beam, the rotation axis of said second rotatable mirror being perpendicular to the rotation axis of said two-sided rotatable mirror.

8. The system defined by claim 1, further comprising:

a second rotatable mirror, for steering the at least one irradiating light beam, located between said irradiating optical system and said two-sided rotatable mirror, wherein the rotation axis of said second rotatable mirror is perpendicular to the rotation axis of said two-sided rotatable mirror;

a third rotatable mirror, for steering the at least one detecting light beam, located between said photodetector and said two-sided rotatable mirror, wherein the rotation axis of said third rotatable mirror is perpendicular to the rotation axis of said two-sided rotatable mirror, wherein said third rotatable mirror rotates simultaneously through the same angle as said second rotatable mirror;

a first relay optical system for making the system pupil conjugate with said second rotatable mirror; and a second relay optical system for making the system pupil conjugate with said third rotatable mirror.

9. An ophthalmic apparatus comprising:

an irradiating optical system comprising at least one light source producing at least one irradiating light beam for irradiating an eye;

an objective lens positioned to receive the at least one irradiating light beam to focus the at least one irradiating light beam on the eye;

a detecting optical system, comprising at least one photodetector, for receiving at least one detecting light beam comprising the at least one irradiating light beam reflected by the eye; and a beam steering optical system, having a system pupil, comprising:

a two-sided rotatable mirror positioned to cover only a first portion of the system pupil and to reflect with a first surface thereof the at least one irradiating light beam received from said irradiating optical system and to reflect to said at least one photodetector with a second surface thereof the at least one detecting light beam reflected by the eye; and beam redirecting means for redirecting one of the at least one irradiating light beam and the at least one detecting light beam;

wherein said irradiating optical system and said at least one photodetector are positioned so that one of the following occurs:

the at least one irradiating light beam is reflected by the first surface of said two-sided rotatable mirror to said beam redirecting means which redirects the at least one irradiating light beam through a second portion of the system pupil not covered by said two-sided rotatable mirror and then through said objective lens to the eye; and the at least one detecting light beam reflected by the eye passes through the second portion of the system pupil not covered by said two-sided rotatable mirror to said beam redirecting means, and is redirected by said beam redirecting means to the second surface of said two-sided rotatable mirror which reflects the at least one detecting light beam to said at least one photodetector, wherein said objective lens makes the pupil of the eye conjugate with the system pupil, wherein said irradiating optical system, said two-sided rotatable mirror, and said objective lens together define an irradiation path for the at least one irradiating light beam;

wherein said objective lens, said two-sided rotatable mirror, and said detecting optical system together define an observation path for the at least one detecting light beam.

wherein said two-sided rotatable mirror steers both the at least one irradiating light beam and the at least one detecting light beam through the same angle when said two-sided rotatable mirror rotates, and wherein the irradiation path and the observation path are spaced from each other at least at the system pupil.

10. The apparatus defined by claim 9, wherein said objective lens receives the at least one detecting light beam reflected by the eye and directs the at least one detecting light beam to the second portion of the system pupil not covered by said two-sided rotatable mirror, and wherein said beam redirecting means is positioned to receive the at least one detecting light beam after passing through the second portion of the system pupil, and redirects the at least one detecting light beam to the second surface of said two-sided rotatable mirror, said second surface of said two-sided rotatable mirror reflecting the at least one detecting light beam to said at least one photodetector, wherein said objective lens, said two-sided rotatable mirror, said beam redirecting element, and said at least one photodetector together define the observation path for the at least one detecting light beam.

11. The apparatus defined by claim 9, wherein said beam redirecting means is positioned to receive the at least one irradiating light beam after being reflected by said first surface of said two-sided rotatable mirror and redirects the at least one irradiating light beam through the second portion of the system pupil to said objective lens, and wherein said irradiating optical system, said objective lens, said two-sided rotatable mirror, and said beam redirecting element together define the irradiation path for the at least one irradiating light beam.

12. The apparatus defined by claim 9, further comprising control means for controlling the rotation angle of said two-sided rotatable mirror in accordance with an output signal from said at least one photodetector to stabilize the position of the at least one irradiating light beam on the eye at least in one dimension when the eye moves.

13. The apparatus defined by claim 9, wherein said at least one light source comprises a first laser emitting a first laser light beam, wherein said irradiating optical system further comprises a second laser emitting a second laser light beam, wherein said irradiating optical system further comprises means for combining the first and second laser light beams into a single combined laser beam and for directing the single combined laser beam to said two-sided rotatable mirror.

14. A beam steering method for steering a beam in a beam steering system having a system pupil, comprising:

a first step of producing at least one irradiating light beam with an irradiating optical system for irradiating an object and projecting the at least one irradiating light beam to a first portion of the system pupil;

a second step of reflecting the at least one irradiating light beam at the first portion of the system pupil with a first surface of a two-sided rotatable mirror to the object;

wherein said first and second steps together define an irradiation path for the at least one irradiating light beam;

a third step of reflecting the at least one irradiating light beam from the object as at least one detecting light beam to a second surface of the two-sided rotatable mirror, and reflecting the at least one detecting light beam from the second surface of the two-sided rotatable mirror to a photodetector;

a fourth step of redirecting one of the at least one irradiating light beam and the at least one detecting light beam;

a fifth step of positioning the irradiating optical system and the photodetector so that one of the following sequences of steps occurs:

reflecting the at least one irradiating light beam with the first surface of the two-sided rotatable mirror, and redirecting the reflected at least one irradiating light beam, reflected by the first surface of the two-sided rotatable mirror, through a second portion of the system pupil not covered by the two-sided rotatable mirror to the object; and projecting the at least one detecting light beam reflected by the object through the second portion of the system pupil not covered by the two-sided rotatable mirror, redirecting the at least one detecting light beam having passed through the second portion of the system pupil to the second surface of the two-sided rotatable mirror, and reflecting the at least one detecting light beam from the second surface of the two-sided rotatable mirror to the photodetector; and a sixth step of steering both the at least one irradiating light beam and the at least one detecting light beam through the same angle when the at least one irradiating light beam is reflected by the first surface of the two-sided rotatable mirror and when the at least one detecting light beam is reflected by the second surface of the two-sided rotatable mirror;

wherein said third step defines an observation path for the at least one detecting light beam, wherein all of the steps of said method are performed so that the irradiation path and the observation path are spaced from each other at least at the system pupil.

* * * * *

UNITED STATES PATENT AND TRADEMARK OFFICE
CERTIFICATE OF CORRECTION

PATENT NO. : 5,633,695
DATED : May 27, 1997
INVENTOR(S) : Feke, et. al.

Page 1 of 3

It is certified that error appears in the above-identified patent and that said Letters Patent is hereby corrected as shown below:

Title page, item:

[57] ABSTRACT

Line 14, "mirror." should read --the mirror.--.

COLUMN 1

Line 24, "More generally, an" should begin as a new paragraph.

Line 67, "two dimensional" should read --two-dimensional--.

UNITED STATES PATENT AND TRADEMARK OFFICE
CERTIFICATE OF CORRECTION

PATENT NO. : 5,633,695
DATED : May 27, 1997
INVENTOR(S) : Feke, et. al.

It is certified that error appears in the above-identified patent and that said Letters Patent is hereby corrected as shown below:

COLUMN 2

Line 7, "(so called" should read --(so-called--.

COLUMN 5

Line 59, "observation" should read --observation path--.

COLUMN 13

Line 41, "①②③" should read -- ①, ②, and ③--.

UNITED STATES PATENT AND TRADEMARK OFFICE
CERTIFICATE OF CORRECTION

PATENT NO. : 5,633,695
DATED : May 27, 1997
INVENTOR(S) : Feke, et. al.

It is certified that error appears in the above-identified patent and that said Letters Patent is hereby corrected as shown below:

COLUMN 15

Line 43, "two dimensional" should read --two-dimensional--.

Line 65, "a" should be deleted.

Signed and Sealed this

Thirteenth Day of January, 1998

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,633,695
DATED : May 27, 1997
INVENTOR(S) : FEKE, ET AL.

It is certified that error appears in the above-identified patent and that said Letters Patent is hereby corrected as shown below:

On the Cover Page

[73] Assignee:

"Canon Kabushiki Kaisha, Tokyo, Japan" should read --The Schepens Eye Research Institute, Boston, Massachusetts, U.S.A. and Canon Kabushiki Kaisha, Tokyo, Japan--.

Signed and Sealed this

Thirtieth Day of June, 1998

Attest:

BRUCE LEHMAN

Attesting Officer     Commissioner of Patents and Trademarks